United States Patent [19]
Tragesser

[11] Patent Number: 5,835,206
[45] Date of Patent: Nov. 10, 1998

[54] USE OF COLOR IMAGE ANALYZERS FOR QUANTIFYING GRAIN QUALITY TRAITS

[75] Inventor: Scott Tragesser, Marshall, Mo.

[73] Assignee: Zenco (No. 4) Limited, London, England

[21] Appl. No.: 651,797

[22] Filed: May 22, 1996

[51] Int. Cl.⁶ .................................................. G01N 21/27
[52] U.S. Cl. .......................................... 356/72; 356/406
[58] Field of Search .................................. 356/72, 406

[56] References Cited

U.S. PATENT DOCUMENTS

| | | |
|---|---|---|
| 3,385,434 | 5/1968 | Nelson . |
| 3,861,788 | 1/1975 | Webster . |
| 3,880,289 | 4/1975 | Gray . |
| 4,260,262 | 4/1981 | Webster ................................. 356/418 |
| 4,436,207 | 3/1984 | Klukis . |
| 4,734,584 | 3/1988 | Rosenthal . |
| 4,806,764 | 2/1989 | Satake . |
| 5,005,774 | 4/1991 | Martin et al. . |
| 5,308,981 | 5/1994 | Perten ................................. 250/339.01 |
| 5,480,354 | 1/1996 | Sadjadi ........................................ 460/7 |

OTHER PUBLICATIONS

Rafael C. Gonzalez and Richard E. Woods, "Digital Image Processing," Library of Congress Cataloging–in–Publication Data, pp. 221–249, *4.6 Color Image Processing*, 1992.

Skye Instruments Incorporated, "SI 700 Leaf Area and Analysis Unit" *Leaf Area and Analysis System Price List*, 1996.

Marvin R. Paulsen, "Machine Vision for Corn Inspection," Grain Quality Conference in Champaign, IL., Mar. 17, 1992, pp. M.1–M.–2.

*Primary Examiner*—Vincent P. McGraw
*Attorney, Agent, or Firm*—B. J. Sadoff; Dana Rewoldt

[57] ABSTRACT

The present invention provides an optical method of analyzing seed quality characteristics such as percent of hard endosperm and seed color utilizing the transmitted visible light, and means to carry out the described method.

8 Claims, 4 Drawing Sheets

USE OF COLOR IMAGE ANALYZERS FOR QUANTIFYING GRAIN QUALITY TRAITS

BACKGROUND OF THE INVENTION

The present invention relates generally to analyzing grain seeds to qualitatively and quantitatively characterize the grain. The present invention provides a method of and apparatus for color image analysis for characterizing multiple grain quality traits in a quantitative manner.

Billions of bushels of grain (corn, soybeans, wheat, sorghum) are grown each year in the United States and enter a distribution network for purchase and utilization by various consumers, including animal feeds, industrial uses and human food processing. Grain varies in its quality and physical attributes from location to location due to genetic differences, local environmental conditions, agronomic production practices and physical handling and shipping treatment. Grains from different locations are combined in large storage and shipping containers for both domestic and export use.

In order to protect the consumer and provide assurances that the product purchased meets consumer needs, the U.S. Congress enacted the United States Grain Standards Act (USGSA) (Aug. 11, 1916, ch. 313, 39 Stat. 453 (7 USC § 71 to 87, 111, 113, 241 to 273, 2209; 16 USC §§ 490, 683) in 1916 to provide a uniform descriptive system for long distance trading of grain. The Federal Grain Inspection Service (FGIS) was created within the U.S. Department of Agriculture (USDA) to: (1) establish uniform Grades and Standards, and (2) to implement nationwide procedures for accurate and unbiased test results. In general, the Grain Standards factors assess physical condition or biological stability of the grain and fall into one of the following five categories:

1. Grade determining: provides a numerical Grade based on the level of the poorest of factors including test weight, heat damage, total damage, broken corn/foreign material (BCFM).
2. Mandatory non-grade determining: grain moisture, broken corn, foreign material.
3. Class: grain color or type—yellow, white, mixed.
4. Special Grade designations: special situations, i.e., insect infestation, type of grain endosperm, i.e., waxy, flint.
5. Optional official criteria: factors requested by party requesting inspection, i.e., protein percent in wheat, which is a measure of end-use value.

See, "Quality Corn; The United States Grades and Standards"; Iowa Corn Growers Association, January, 1990, No. 2 of 6.

Since the inherent quality of grains are not routinely measured and included in the USGDS, end-users have set their own internal standards to assure the grain purchased for their processing needs provides the greatest efficiency and return. Such factors may include, but are not limited to, color, percent protein, oil, starch and hard endosperm. These traits are of particular interest to wet and dry millers of corn.

Wet millers process grain by steeping the grain in liquid(s) of varying composition to extract the starch, protein, gluten, oil, and hulls. Starch is further processed for various industrial starch uses, or converted into sweeteners or alcohol. Protein and gluten fractions are generally sold as animal feeds.

Dry millers process grain by mechanically breaking and separating the grain fractions through a series of rollers and shakers into the various sized components. Based on size and composition, these components are referred to as grits, meal, flour, germ and bran. These fractions are purchased by end-users for processing into cereals, snack foods, baking products, brewing and other industrial uses. Larger grit particle size is of the greatest value. A variant of dry milling is alkaline-cooking which produces dry masa flour for Mexican foods such as tortillas and snack foods.

In recent years, the ability to identify, preserve, ship and distribute grains with specific traits of added value to the seedsman, the grower and the end-user has increased interest in a systematic means of consistently characterizing grain for those specific traits of interest. Further, plant breeders need quick, accurate, reliable analysis methods on which to base individual plant selections in their breeding schemes. Two traits of particular interest to both wet and dry millers, and thus plant breeders, are color and relative percentages of hard and soft endosperm. The preferences depend on the product manufactured by the end-user.

White corn processors prefer a "clean" white, without tones of yellow, red or a "dirty" (i.e., gray) cast. Yellow food corn processors prefer a "bright, medium-yellow" color. As the descriptions suggest, color ratings are highly subjective. Some analyses attempt to compare grain to a standard color chart, e.g., Hunter Color Scale, to evaluate grain (see, "Intrinsic Value of Nebraska Corn: 1994 Crop Year Report"; Jackson, Nebr. Corn Board, P.O. Box 95107, 301 Centennial Mall South, Lincoln, Nebr. 68509-5107); but more often ratings over a scale of 1–5 are given based on the expertise of the observer. Ratings of 4–5 are too dark, and 1–2 may be too light or pale in color. Unacceptable color results in products which have unsatisfactory consumer acceptance. To date, seed color rating continues to rely on this subjective analysis.

Quantitative characteristics of grain seed including protein, oil and starch content as well as methods of qualitatively distinguishing between seed types have been available for some time. Examples of these methods are described in Nelson (U.S. Pat. No. 3,385,434; Gray (U.S. Pat. No. 3,830,289; Webster (U.S. Pat. No. 4,260,262; and Rosenthal (U.S. Pat. No. 4,734,584).

Nelson teaches a method of sorting seed corn from field corn based on the transluminescent characteristics of each. The apparatus described by Nelson contains a strong light beamed from multiple directions against the kernels of corn in a manner which allows for detection and comparison of reflected and transluminescent light. Nelson then sorted the kernels according to their transluminescent characteristics while ignoring the surface reflected light.

Gray teaches that Nelson's method is relatively unreliable in practice because of the unpredicted effects of reflected radiation and because of the size difference of the seed corn kernels. Gray provides an improved sorting method based on measuring and comparing the shadow pattern of at least two areas of light attenuation through a seed. Neither Gray nor Nelson teach the existence of a correlation between hard endosperm percent and the amount of transmitted light or a manner of calculating same.

Webster describes the use of photo-optical grain quality analyzers which calculates seed characteristics, such as oil percentage, water percentage, and protein percentage, from measurement of reflected infra-red light.

Rosenthal provides an apparatus for near infra-red illumination of seeds and detection of reflected light from same for calculation of seed characteristics.

More recently, Paulsen (Machine Vision for Corn Inspection, Abstract of presentation at the 1992 Grain Quality Conference in Champaign, Ill. (Mar. 17, 1992)) described a machine vision system containing an image processing board, a microcomputer with monitor, a display monitor, a solid state CCD camera, and a lighting chamber for holding samples. Paulsen describes the following four applications for his system which include measurement of kernel length, detection of stress cracks in kernels, detection of cracks in the pericarp with the use of dye staining and distinguishing between whole and broken kernels. Paulsen states that development of his system is continuing in an effort to detect corn color and kernel hardness. The Abstract does not include a detailed description of how to repeat Paulsen's work or detailed results of the accuracy or reliability of the methods employed.

One of skill in the art will appreciate that a corn kernel consists of a germ (embryo) and endosperm covered by a seed coat or pericarp. The germ is the major oil source within the kernels and accounts for about 12% of the kernel. Approximately 70% of the kernel consists of endosperm or the starch component of the grain with some associated protein. The makeup of the endosperm determines the processing usage of the grain. Endosperm consists of varying percentages of soft and hard endosperm. Generally, soft endosperm grains are preferred by wet millers and hard endosperm grains are preferred by dry millers. Starch is typically more easily extracted from soft endosperm grain types. Hard endosperm kernels produce larger grit components, which are more valuable, with less loss than the soft (flour) endosperm component. Endosperm hardness has been measured in several ways including visual observation of individual kernels and a floaters test based on density of the kernel.

Visual observation of grain over a light box and a subjective rating given by an experienced person has long been a common screening method. Soft endosperm is more opaque and does not transmit light, while hard endosperm is more translucent and transmits more light. Such ratings depend on the "eye of the beholder" and vary based on the person rating the grain, so that hybrids acceptable for one processor may not be acceptable to another. In a breeding program to improve grain texture, high data variability occurs due to multiple raters, or a single person bears the burden of observing and rating thousands of samples to minimize such variation. Even then, variation occurs due to fatigue and observer errors.

The floaters test is commonly used as an indirect measure of kernel hardness, but is actually a measure of the uniformity of the grain in regard to density. In this test, the number of kernels which float in a 1.275 specific gravity solution are counted. Processors generally specify a maximum percent floaters allowable. This is a fairly time consuming process of counting a given number of kernels per sample, involving placing the kernels in the solution, counting and removing same from the solution.

In recent years, scientists and end-users have attempted to quantify hardness more objectively. A hardness index using a tangential abrasive dehulling device (TADD) is utilized for the Texas Foodcorn Performance Test, as described by Bockholt et al (1995 Texas Food Corn Performance Test; The Texas Agricultural Experiment, Station/Department of Soil & Crop Sciences, Texas A&M University, College Station, Tex. In this test, the amount of material removed, expressed as a percentage of the total sample, is related to the relative proportions of hard to soft endosperm, kernel size and shape, and type of denting. It requires 45 gm of whole kernels and is a destructive technique. Seeds cannot be later used for any purpose, which is a major drawback in a breeding program, where it is desirable to select and plant the best kernels.

Near-infrared transmittance of seed has also been used to measure the density of individual corn seeds as an estimate of hardness. "Average" corn has a density of 1.26–1.27 gm/cc, while corn above 1.30 gm/cc is considered very hard. While this test reasonably predicts overall kernel hardness, it does not provide information on the relative amounts of hard and soft endosperm to the processor.

The presently available methods for evaluating quality traits of corn grain such as color and percent hard endosperm are, at worst, subjective, variable and dependent on the skilled "eye" of the beholder, and, at best, a measure of kernel parameters which indirectly predict endosperm hardness. In all cases, a given test only measures one trait and there is no analysis which measures multiple quality traits.

SUMMARY OF THE INVENTION

It is an object of the present invention to provide a method of analyzing corn seed characteristics.

Another object of the invention is to provide an apparatus of color imaging software and hardware, which has been modified by including two sets of polarizing lenses interposed between the light source and an imaging camera so the color imaging apparatus can be used to characterize multiple grain quality traits in a quantitative manner.

In the method of the present invention, light is directed through a first linear polarizing light filter and through a seed sample. Light transmitted through the seed sample is collected by a video camera after having passed through a second linear polarizing light filter which is positioned to have its polarizing lines 90° from the first filter.

Light received through this second filter and the video camera lens is transmitted to a computer. Data from the light is recorded for each of the colors red, green and blue as well as grey from which analysis and calculations are made to determine the color (hue), the whiteness (saturation), the brightness (intensity), and the hard endosperm percentage. In addition, using a standard number of kernels per sample, the average kernel size is calculated. Further, the relative grit size can be predicted from the percent hard endosperm and kernel size. It is a further object of the present invention to provide a method for breeding and identifying improved food and industrial corn hybrids through the use of the disclosed method which produces an objective measure of seed quality.

The present invention provides a method of analyzing seed quality which includes the steps of measuring the visible light transmitted through at least one seed and analyzing the transmitted light to estimate the quality of the seed. In the exemplified embodiment, the seed is corn and the analysis includes measurement of at least one of the percentage of hard endosperm of the seed, and the color of the seed, as expressed in hue, saturation and intensity. The method of the present invention may also be used to measure the kernel area of the seed.

Since the present invention is not destructive of seed being analyzed, the method of the present invention can be used for selecting for traits of the seeds from a breeding population. Additionally, the present invention can be used and employed not only when the kernel is from a commercial hybrid but during the breeding and research portion of developing a commercial hybrid having the desired seed traits. The seeds can be analyzed for HE%, color, etc, as described herein, and the results of same can be used in breeding for complementary traits. That is, for example, if an inbred has an excellent HE% and an acceptable white color or average white color as analyzed by the presently disclosed method then it can be crossed with a second inbred which would have an excellent white color and an equal or slightly lower HE-. Then the breeder will self pollinate plants to develop progeny which would be segregating for the various traits and analyze the progeny seed to select for the seed that shows at least one of the desired color, HE% or kernel area; preferably the seed that shows the desired color and HE%.

It is an object of the present invention, therefore, to provide a method of breeding corn which includes the steps of analyzing corn seed by the method described herein and selecting corn seed with at least one desirable trait selected from hard endosperm content or color; breeding the selected corn seed such that progeny are produced; and analyzing the progeny for the selected desirable trait. Breeding of the present method may include inbreeding or cross-breeding and analysis of the progeny may include conventional methods or the method of the present invention. Production and analysis of the progeny is not limited to first generation progeny.

In a further embodiment, the present invention provides an apparatus with illumination means for illuminating at least an individual seed with visible light, means to measure the visible light transmitted through an illuminated seed; means to analyze the measured visible light to calculate at least one of the hard endosperm content of the seed, the hue, saturation or intensity of the color of the seed, and the kernel area of the seed; and, optionally, means for sorting seeds based, at least in part, on the analysis.

These and other objects of the invention will be understood by a person of skill in the art upon a review of the specification, associated drawings and appended claims.

DETAILED DESCRIPTION OF THE DRAWINGS

Figure 1:
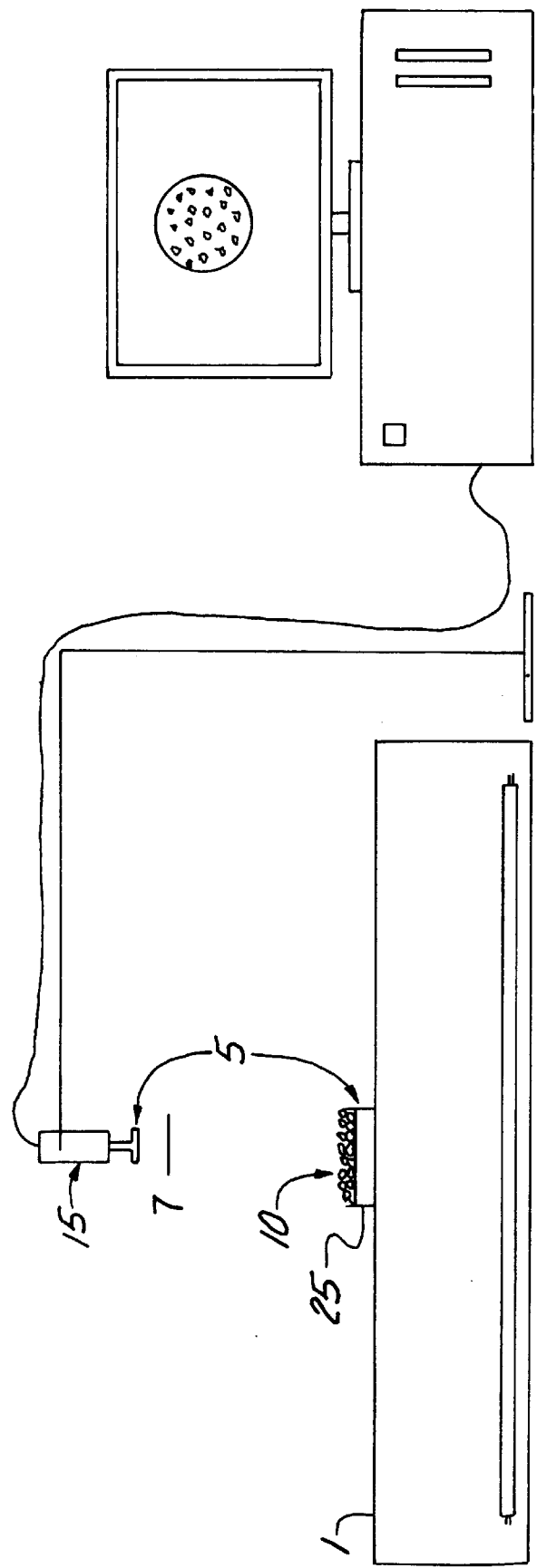
FIG. 1 schematically demonstrates the test equipment used to exemplify the presently disclosed method.
Figure 2A:
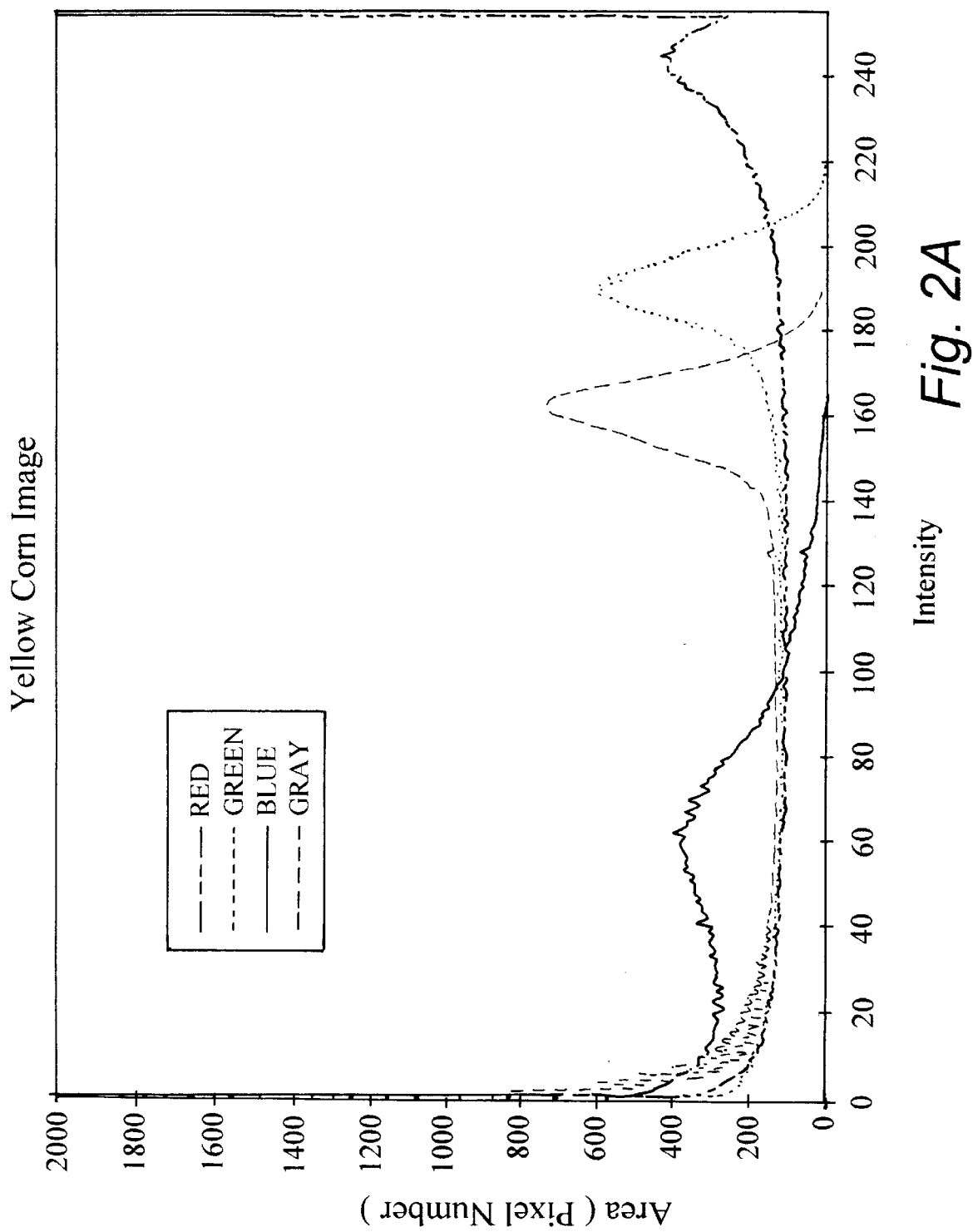
FIGS. 2A and 2B are sample histograms of a kernel measured according to the present method.
Figure 2B:
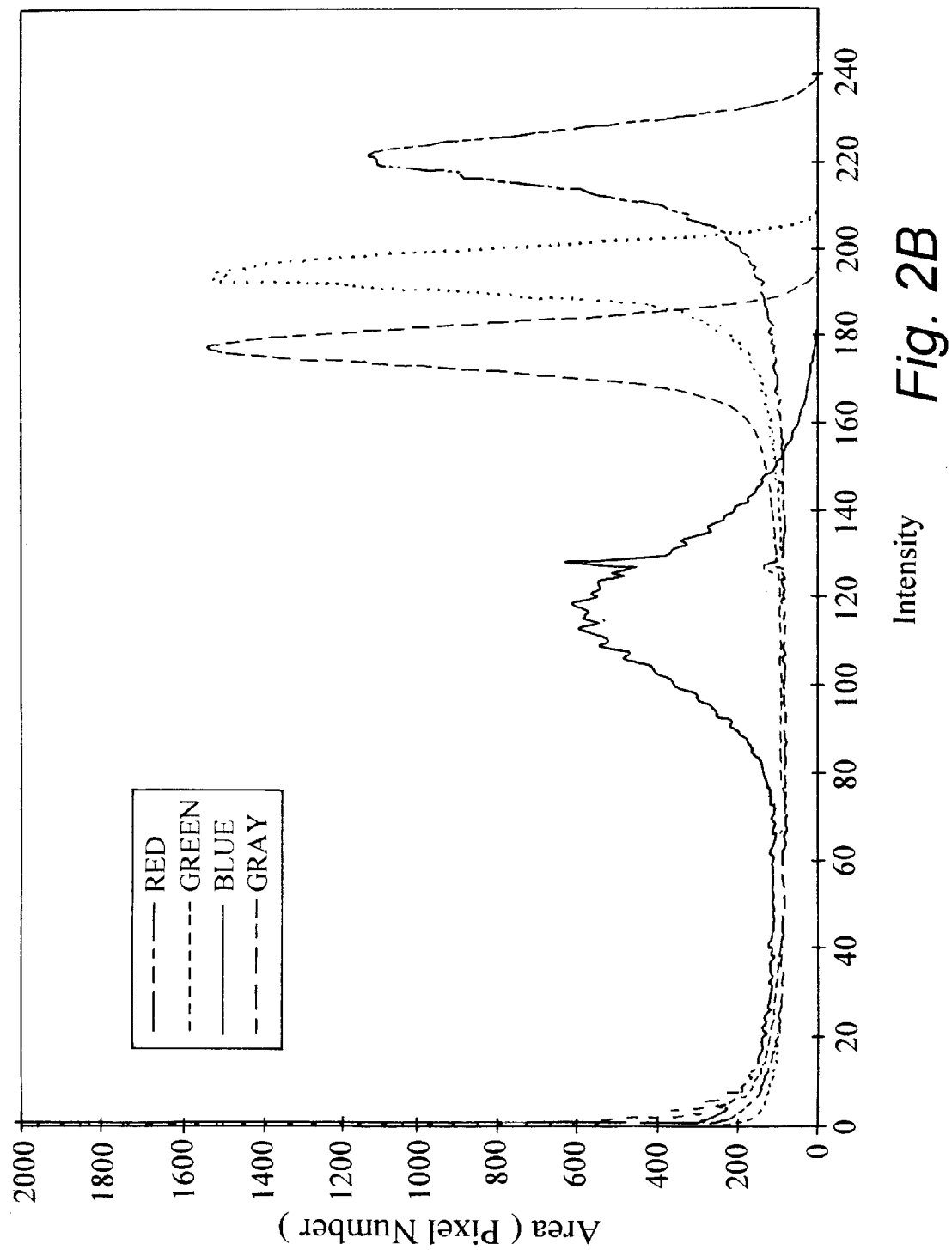

The present invention provides an objective analysis of color and hard endosperm percent of seeds, preferably corn seeds. The applicant has appreciated that known optical techniques utilizing infra-red and near-infra-red reflective measurements are not ideal for corn measurements due to the variable gloss of corn seeds. The presently disclosed techniques, although expected to be applicable to a number of types of seeds, is expected to be particularly advantageous for seeds bearing a highly reflective coat.

The method of the present invention entails capturing the image of at least one kernel by means known in the art. See, for example, Skye Instruments Ltd., Unit 5, Ddole Ind. Estate, Llandrindod Wells, Powys LD16DF UK SI7100 Catalog and Data Translation®, 1993 Applications Handbook Volume 2, Number 1, Data Translation, Inc., 100 Locke Dr., Marlboro, Mass. 01752-1192. The applicant has found it advantageous, however, to modify the commercially available system to reduce background light by including a pair of polarized lenses positioned 90° to each other such that the grain sample is placed between the cross-polarizing filters. Conventional computer software is used in the method of the present invention to produce a histogram of the number of pixels illuminated for a given intensity of light detected by the camera for each color red, green, blue and grey. The histogram data is used, either immediately or at a later time, to determine the grain color and percent hard-endosperm (HE%) of the analyzed gain(s) in a manner described below.

The area under the largest peak of number of pixels in each histogram is used in the present invention to calculate the percent hard endosperm and the color of the kernel or kernels under investigation.

In calculating the HE%, each histogram is analyzed to calculate the slope of the curve (number of pixels/intensity) at each intensity using five intensity points on each side of the point being estimated. Slope may be determined by any of a number of known means, the exemplified system of the presently disclosed method utilized a commercially available spreadsheet programs (i.e., Microsoft Excel). The slope values are then used to identify that portion of the histogram which contains the major peak by discriminating those slopes which are at least a discernable proportion of the maximum. In a preferred embodiment of the disclosed method, 10% of the maximum positive slope has been used as a cut-off point. The present method defines the hard endosperm area of the kernel as corresponding to the area under the histogram for those intensities greater than the intensity corresponding to the slope which is greater than 10% of the maximum positive slope. In determining the maximum positive slope of yellow corn, the large positive slope on the extreme right of the red histogram has been ignored.

The average intensity of the hard endosperm area is then calculated for each color, (red, green, blue and grey) independently by calculating a weighted average intensity where the number of pixels is the weighting factor as expressed in the following:

$$\text{weighted average intensity} = (\Sigma I_i P_i)/(\Sigma P_i)$$

where $I_i$=ith intensity for hard endosperm region
$P_i$=number of pixels recorded for ith intensity.

The percentage of hard endosperm is calculated from the gray image by dividing the sum of pixels in the hard endosperm region by the sum of all pixels of measurable intensity. That is, pixels where the intensity is zero are ignored in the hard endosperm calculation.

In expressing the color of the seeds, the primary colors, red, green and blue, are translated into hue, intensity and saturation where hue is the actual color of the Sample as would be seen by the human eye. Hue is reported as an angle from zero degrees with reference to red being 0°, green being 120°, and being blue being 240°. Saturation is the purity of the hue that is being scanned where 100% is the maximum saturation of the hue and 0% is the minimum. Intensity is an estimate of the gray-level of the hard endosperm.

The average intensity of the individual colors (red, green, blue) are used to obtain the hue, saturation and intensity data (HSI) from relationships known in the art. Briefly, intensity at any given pixel is expressed as:

$$I = \frac{R+B+G}{3}$$

Hue is given by:

$$H = (1/360)[90 - \arctan(F/\sqrt{3}) + \{0, G>B; 180, G<B\}]$$

where $$F = \frac{2R - G - B}{G - B}$$

and saturation is expressed as:

$$S = 1 - \left[ \frac{\min(R,G,B)}{I} \right].$$

Further explanations of these calculations are available, for example, in the 1993 Applications Handbook published by Data Translation, Inc. and Gonzalez et al, Digital Image Processing, Addison-Wesley Publishing Co., Reading, Mass. (1993), especially, pages 221–248. In the presently exemplified embodiment of the present invention, the Hue calculation has been modified by deleting the 1/360 portion of the equation; in this way, the hue is reported as an angle rather than a number from zero to one. Also, it was required by Microsoft Excel software that any arctangent be multiplied by 180/pi.

The present invention may also be used to analyze relative kernel size by placing a known number of kernels in the area of the image captured and calculating the sum of the pixels with a measurable intensity divided by the sum of all pixels. This estimation is expressed as the percentage of kernel coverage over the total area viewed by the camera and can be reported on a per kernel basis if different kernel numbers are used for different samples, or, on a whole sample basis if all samples contain the same number of kernels.

Moreover, relative grit size may be expressed as the product of the hard endosperm percentage and the relative size.

The following non-limiting example illustrates the present invention.

EXAMPLE

Equipment (Numerical designations are references to FIG. 1):

- SI 700 Leaf Area and Analysis Unit from Skye Instruments Incorporated (P.O. Box 1988, Perkasie, Pa. 18944) which includes a fluorescent light box of variable intensity (1), Vidicom Camera (15), (625 lines) with 16 mm F.28 lens, digitizing electronics unit, computer interface card Skye image analysis software;
- Compaq 380/33 m with an NEC Multisync 3FGe monitor
- Polarizing filter—linear polarized filter are placed such that the polarizing lines are 90° to each other. The lower lens (25) is positioned to hold sample grain while the upper polarizer (1) can be placed anywhere between the sample and the camera (5).

Procedure:

Rather than determine the 10% maximum of slope for each color for each sample, an average profile was established by averaging the histogram data for each color across all 60 white corn and 60 yellow corn samples initially tested. From this average color file, the 10% maximum slope of each color has been determined and these points have been used on all samples.

Average color files can be produced in this way after each run or lot of new samples, or whenever appropriate. Updates are preferred at least yearly if average color files are to be routinely used. White and yellow corn color files are kept separate as the characteristics of each are distinct.

Hard Endosperm:

The hard endosperm percentage estimation, as related above, was tested against a known standard test performed by the Illinois Crop Improvement Association (ICIA). At ICIA, a sample of 20 kernels is viewed over a light table one kernel at a time and scored from 70 to 100 in increments of five. The 20 scores are averaged to obtain a sample score. A total of 21 grain samples were chosen for this comparison. Seven samples with high HE%, 7 samples with intermediate HE%, and 7 samples with low HE% were selected from a given quality database to be scored by both the ICIA method and the method of the present invention. In the method of the present invention, each sample of 20 kernels was captured by the camera three times with the sample being removed and replaced before each image capture. The same 20 kernels were then sent to ICIA for their visual rating.

Figure 3:
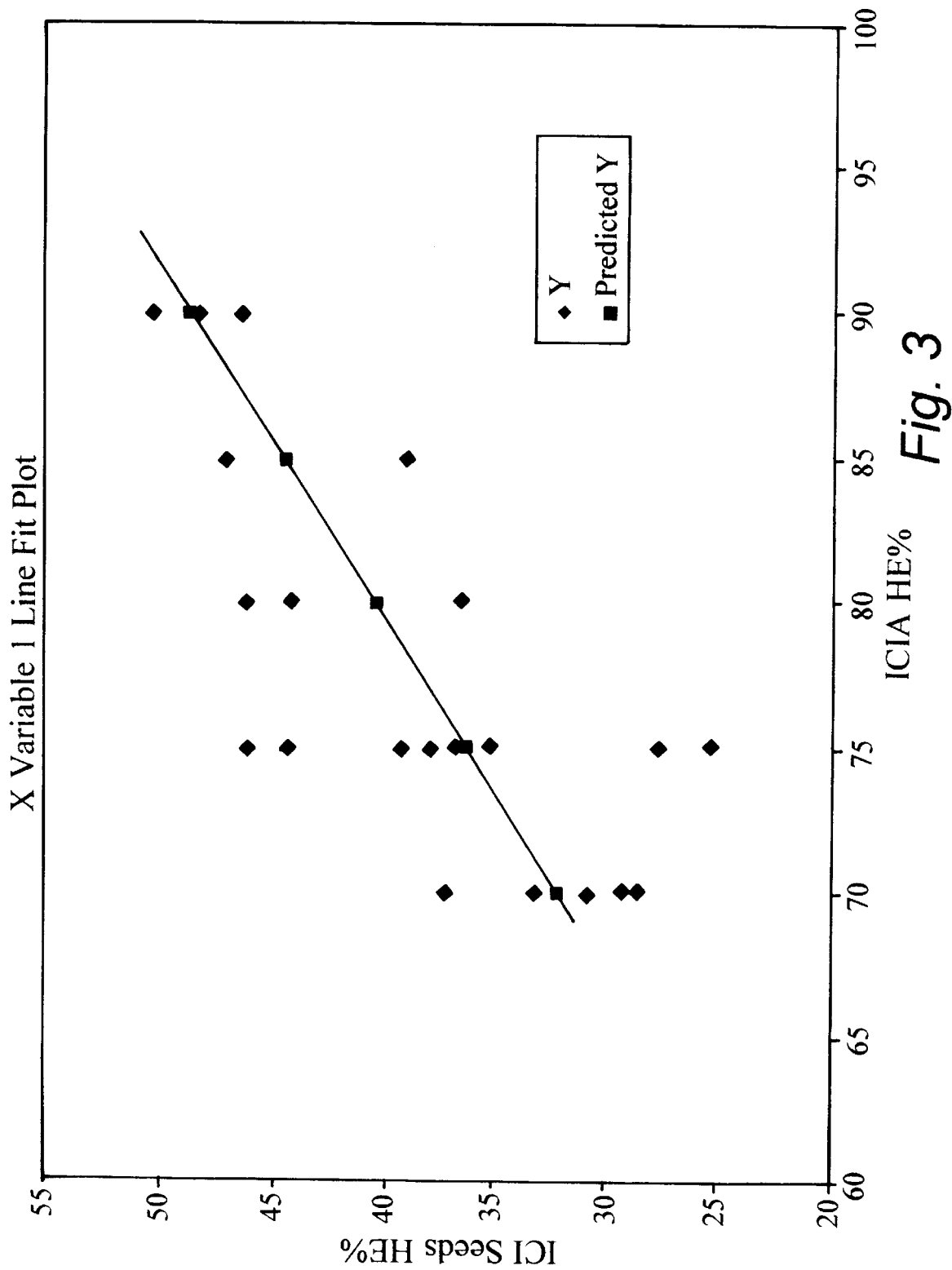
FIG. 3 is a graph showing results from experiments comparing the presently disclosed method to that of a commercially available method, as described herein.

Pearson correlations and Spearman rank correlations were performed on the data. Both correlations were highly significant (Prob>|R|=0.0001) with correlation values of 0.74 for the Pearson correlation and 0.76 for the Spearman rank correlation. FIG. 3 shows a plot of the present invention HE% v. ICIA HE% with a predicted regression line plotted in the middle.

Color:

The method of the present invention was used to analyze thirty-two yellow and forty white corn samples with the results given in Tables 1 and 2 below. One skilled in the art will appreciate that the objective method of the present invention provides end-users the ability to more clearly discriminate seed color, thus providing a more uniform and higher quality product. Similarly, breeders may use the presently disclosed method to evaluate research programs designed to improve the quality and uniformity of seed color.

TABLE 1

YELLOW CORN

| SAMPLE | HUE | SAT | INT | HE % | KERNEL AREA % |
|---|---|---|---|---|---|
| RANGE | 0–360 | 0–100 | 0–255 | 0–100 | 0–100 |
| 1 | 43.9 | 0.56 | 164.9 | 0.45 | 0.54 |
| 2 | 44.0 | 0.56 | 164.3 | 0.47 | 0.60 |
| 3 | 43.5 | 0.55 | 165.1 | 0.45 | 0.58 |
| 4 | 43.8 | 0.56 | 165.4 | 0.48 | 0.55 |
| 5 | 43.4 | 0.55 | 165.0 | 0.42 | 0.58 |
| 6 | 43.3 | 0.56 | 165.1 | 0.44 | 0.58 |
| 7 | 43.4 | 0.57 | 163.7 | 0.44 | 0.61 |
| 8 | 43.6 | 0.55 | 165.4 | 0.46 | 0.57 |
| 9 | 44.6 | 0.57 | 164.3 | 0.45 | 0.59 |
| 10 | 43.3 | 0.56 | 163.9 | 0.39 | 0.60 |
| 11 | 43.2 | 0.57 | 164.7 | 0.48 | 0.58 |
| 12 | 43.6 | 0.56 | 165.8 | 0.50 | 0.56 |
| 13 | 43.8 | 0.55 | 164.8 | 0.42 | 0.61 |
| 14 | 44.5 | 0.58 | 164.9 | 0.50 | 0.57 |
| 15 | 42.8 | 0.55 | 165.6 | 0.45 | 0.52 |
| 16 | 46.0 | 0.57 | 164.8 | 0.51 | 0.56 |
| 17 | 42.7 | 0.56 | 164.5 | 0.39 | 0.61 |
| 18 | 42.2 | 0.55 | 164.2 | 0.38 | 0.60 |
| 19 | 42.9 | 0.55 | 165.0 | 0.41 | 0.57 |
| 20 | 43.8 | 0.56 | 165.0 | 0.48 | 0.54 |
| 21 | 44.7 | 0.55 | 164.7 | 0.39 | 0.58 |
| 22 | 44.2 | 0.55 | 164.9 | 0.44 | 0.59 |
| 23 | 44.8 | 0.55 | 165.5 | 0.44 | 0.57 |
| 24 | 44.4 | 0.54 | 164.5 | 0.41 | 0.58 |
| 25 | 44.4 | 0.55 | 165.0 | 0.45 | 0.57 |
| 26 | 44.9 | 0.53 | 164.6 | 0.37 | 0.61 |
| 27 | 44.4 | 0.56 | 165.1 | 0.51 | 0.55 |
| 28 | 43.8 | 0.57 | 164.2 | 0.44 | 0.62 |
| 29 | 43.0 | 0.55 | 164.7 | 0.43 | 0.60 |
| 30 | 43.9 | 0.57 | 165.1 | 0.46 | 0.59 |
| 31 | 45.0 | 0.57 | 165.4 | 0.49 | 0.56 |
| 32 | 44.9 | 0.53 | 166.1 | 0.46 | 0.56 |
| AVG. | 43.9 | 0.56 | 164.9 | 0.45 | 0.58 |
| STD. | 0.41 | 0.02 | 0.6 | 0.05 | 0.03 |

TABLE 1-continued

YELLOW CORN

| SAMPLE | HUE | SAT | INT | HE % | KERNEL AREA % |
|---|---|---|---|---|---|
| C.V. | 0.94 | 3.18 | 0.3 | 10.5 | 4.76 |
| LSD | 0.83 | 0.04 | 1.1 | 0.09 | 0.06 |

TABLE 2

WHITE CORN

| SAMPLE | HUE | SAT | INT | HE % | KERNEL AREA % |
|---|---|---|---|---|---|
| RANGE | 0–360 | 0–100 | 0–255 | 0–100 | 0–100 |
| 1 | 45.7 | 0.34 | 174.9 | 0.48 | 0.52 |
| 2 | 46.1 | 0.31 | 176.0 | 0.43 | 0.54 |
| 3 | 46.2 | 0.32 | 175.9 | 0.50 | 0.51 |
| 4 | 45.6 | 0.30 | 177.2 | 0.47 | 0.52 |
| 5 | 46.4 | 0.32 | 175.8 | 0.45 | 0.55 |
| 6 | 45.7 | 0.29 | 177.1 | 0.39 | 0.54 |
| 7 | 47.0 | 0.31 | 175.9 | 0.50 | 0.51 |
| 8 | 46.1 | 0.33 | 176.0 | 0.51 | 0.52 |
| 9 | 47.0 | 0.32 | 175.3 | 0.47 | 0.54 |
| 10 | 46.7 | 0.29 | 176.4 | 0.40 | 0.58 |
| 11 | 45.5 | 0.28 | 177.2 | 0.37 | 0.55 |
| 12 | 46.6 | 0.33 | 175.2 | 0.51 | 0.54 |
| 13 | 46.9 | 0.32 | 175.8 | 0.52 | 0.51 |
| 14 | 46.0 | 0.33 | 175.3 | 0.49 | 0.54 |
| 15 | 45.6 | 0.31 | 176.5 | 0.47 | 0.55 |
| 16 | 46.7 | 0.33 | 175.1 | 0.47 | 0.55 |
| 17 | 45.7 | 0.29 | 176.9 | 0.39 | 0.56 |
| 18 | 45.9 | 0.30 | 178.5 | 0.46 | 0.55 |
| 19 | 45.7 | 0.32 | 175.7 | 0.47 | 0.54 |
| 20 | 46.3 | 0.32 | 176.2 | 0.50 | 0.52 |
| 21 | 46.6 | 0.32 | 175.7 | 0.43 | 0.56 |
| 22 | 46.5 | 0.33 | 175.4 | 0.47 | 0.53 |
| 23 | 46.4 | 0.32 | 175.6 | 0.38 | 0.57 |
| 24 | 46.9 | 0.29 | 176.3 | 0.38 | 0.58 |
| 25 | 46.0 | 0.33 | 175.8 | 0.52 | 0.52 |
| 26 | 46.3 | 0.32 | 175.6 | 0.42 | 0.56 |
| 27 | 46.4 | 0.33 | 176.0 | 0.50 | 0.52 |
| 28 | 46.0 | 0.30 | 176.2 | 0.38 | 0.57 |
| 29 | 44.9 | 0.31 | 177.1 | 0.48 | 0.51 |
| 30 | 46.2 | 0.30 | 176.3 | 0.38 | 0.58 |
| 31 | 44.9 | 0.35 | 175.5 | 0.55 | 0.49 |
| 32 | 46.0 | 0.29 | 177.0 | 0.40 | 0.55 |
| 33 | 45.2 | 0.32 | 176.5 | 0.47 | 0.50 |
| 34 | 45.7 | 0.34 | 175.4 | 0.50 | 0.52 |
| 35 | 46.9 | 0.33 | 175.1 | 0.46 | 0.56 |
| 36 | 46.7 | 0.30 | 176.4 | 0.52 | 0.53 |
| 37 | 46.2 | 0.31 | 176.5 | 0.57 | 0.50 |
| 38 | 46.4 | 0.32 | 176.1 | 0.57 | 0.51 |
| 39 | 46.3 | 0.36 | 174.1 | 0.56 | 0.53 |
| 40 | 45.2 | 0.30 | 177.1 | 0.48 | 0.52 |
| AVG. | 46.1 | 0.32 | 176.0 | 0.47 | 0.54 |
| STD. | 0.60 | 0.01 | 0.8 | 0.04 | 0.02 |
| C.V. | 1.29 | 4.74 | 0.4 | 8.55 | 3.29 |
| LSD | 1.19 | 0.03 | 1.5 | 0.08 | 0.04 |

All publications mentioned hereinabove are hereby incorporated in their entirety by reference.

While the foregoing invention has been described in some detail for purposes of clarity and understanding it will be appreciated by one of ordinary skill in the art from reading this disclosure that various changes in form and detail can be made without departing from the true scope of the present invention and appended claims.

What claimed is:

1. An optical method of analyzing seed quality comprising:

illuminating said seed with visible polarized light, measuring cross polarized light transmitted through said seed;

analyzing said cross polarized transmitted light to estimate the quality of said seed, whereby reducing background light.

2. The optical method of claim 1, wherein said seed is corn.

3. The optical method of claim 1 wherein said analysis comprises estimating the percentage of hard endosperm of said seed.

4. The optical method of claim 1, wherein said analysis comprises calculating at least one of the hue, saturation and intensity of the color of said seed.

5. The optical method of claim 1, wherein said analysis comprises calculating the kernel area of said seed.

6. A method of breeding corn comprising the steps of:

analyzing corn seed by the method of claim 1 and selecting corn seed with at least one desirable trait selected from hard endosperm content or color;

breeding said corn seed such that progeny is produced; and analyzing said progeny for said at least one desirable trait.

7. The method of claim 6 wherein said breeding is either inbreeding or cross-breeding.

8. In an apparatus for analyzing seeds, the improvement comprising:

means to illuminate at least an individual seed with visible polarized light;

means to measure the visible polarized light transmitted through said seed;

means to analyze the detected light to calculate at least one characteristic of said seed selected from the group consisting of the hard endosperm content of the seed, the hue, saturation or intensity of the color of the seed, and the kernel area of the seed; and, means for sorting seeds based on said calculated characteristic.

* * * * *